United States Patent
Dye

(10) Patent No.: US 6,855,149 B2
(45) Date of Patent: Feb. 15, 2005

(54) POSTERIOR RETRACTOR AND METHOD OF USE FOR MINIMALLY INVASIVE HIP SURGERY

(75) Inventor: Donald Dye, Pflugerville, TX (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/375,395

(22) Filed: Feb. 27, 2003

(65) Prior Publication Data

US 2004/0172038 A1 Sep. 2, 2004

(51) Int. Cl.[7] ............................................. A61B 17/58
(52) U.S. Cl. ........................................ 606/90; 600/210
(58) Field of Search ........................... 606/86, 91, 105, 606/90; 623/22.12; 600/210

(56) References Cited

U.S. PATENT DOCUMENTS

| | | | | |
|---|---|---|---|---|
| 2,695,607 A | * | 11/1954 | Hipps et al. ................. | 600/210 |
| 3,651,800 A | * | 3/1972 | Wilbanks ..................... | 600/210 |
| 4,048,987 A | * | 9/1977 | Hurson ......................... | 600/206 |
| 4,686,972 A | * | 8/1987 | Kurland ........................ | 606/96 |
| 4,936,863 A | * | 6/1990 | Hofmann .................. | 623/23.26 |
| 4,995,875 A | * | 2/1991 | Coes ............................. | 606/90 |
| 5,303,694 A | * | 4/1994 | Mikhail ....................... | 600/214 |
| 6,315,718 B1 | * | 11/2001 | Sharratt ....................... | 600/228 |
| 2002/0026245 A1 | * | 2/2002 | Malawer ................... | 623/23.43 |

\* cited by examiner

*Primary Examiner*—Kevin P. Shaver
(74) *Attorney, Agent, or Firm*—Jonathan D. Feuchtwang; Zimmer Technology, Inc.

(57) ABSTRACT

A method and apparatus for performing minimally invasive hip surgery for implanting a prosthetic acetabular component into a natural acetabulum. The method and apparatus include a posterior retractor having handle and retracting sections. The retracting section retracts soft tissue in the posterior section of the surgical site and includes a paddle with a curved flare and an elongated curved prong extending outwardly.

20 Claims, 3 Drawing Sheets

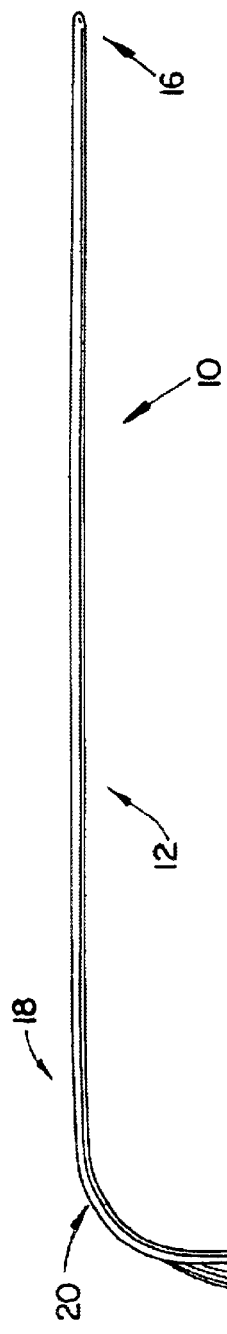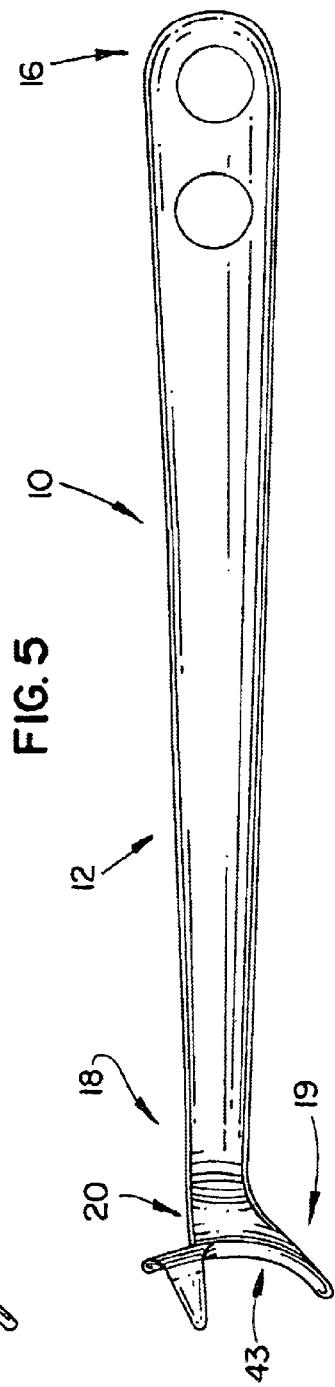

POSTERIOR RETRACTOR AND METHOD OF USE FOR MINIMALLY INVASIVE HIP SURGERY

FIELD OF THE INVENTION

The disclosure herein generally relates to a method and apparatus for performing minimally invasive hip surgery and, more particularly, to an improved method and apparatus for performing minimally invasive hip replacement surgery for the acetabulum using a posterior retractor instrument.

BACKGROUND OF THE INVENTION

Traditional hip replacement surgery has been used in the United States since as early as the 1960's. The surgical technique to implant a hip has not drastically changed over the years, and today, this technique is quite successful. In fact, the surgical technique is prolifically used throughout the world and has a known success rate of over 90%. Certainly, the traditional surgical technique is fundamentally sound and predictable.

Unfortunately, traditional techniques to implant a hip have well recognized shortcomings. Most importantly, a rather large incision is made on the side of the hip. The incision can extend from 6 to 12 inches; the actual length of the incision depends on the size of the patient and type of surgery (revision versus total hip arthroplasty, for example). A long, deep incision can divide a number of important stabilizing muscles and tendons and further damage the hip joint and surrounding soft tissue. Inevitably, long incisions lead to larger blood losses, longer rehabilitation times for patients, and unsightly scar lines. A patient can easily spend four or five days in the hospital after a total hip arthroplasty, for example.

Recently, surgeons have been developing new, less invasive surgical techniques to perform total hip arthroplasty and revision hip surgery. Minimally invasive surgery, or MIS, is one such technique with great promise to become a popular and accepted technique for implanting a hip.

MIS has significant advantages over traditional hip replacement surgery. Most importantly, a rather small incision is made on the side on the hip. This incision is approximately 3 to 5 inches long, and the benefits of a shorter incision are enormous.

First and foremost, the patient can recover in a much shorter period of time after a MIS. The recuperation time in the hospital can be a few days and significantly reduce the cost to both the patient and hospital. In fact, some patients are leaving the hospital within 24 to 48 hours after the surgery. Obviously, this shortened time period is extremely important to the patient.

As another advantage, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Presently, instruments to perform MIS are being developed and refined. These instruments have a vital role in the ability to perform a successful minimally invasive surgery. These instruments, for example, must enable the surgeon to place the hip implant in a very precise location. If the implant is not accurately placed, then complications, such as dislocation or subluxation, can occur. Further and most importantly, the instruments must consistently and reliably perform through a small three inch opening in the patient.

A successful design of instruments for MIS has other challenges as well. Specifically, the instrument must be easy to use and facilitate the implantation procedure. If the MIS instrumentation is too cumbersome or not easy to manipulate, then the surgeon will be less likely to use minimally invasive surgery. The patient, then, will not reap the benefits MIS has to offer.

As yet another consideration, MIS instrumentation must appeal to a wide range of orthopedic surgeons with various skills and experience. If, for example, the instruments are too complex and complicated, then they will not be appealing and accepted in the orthopedic surgical community. Further yet, the training and skill level required to use the instruments and become proficient with them, cannot be overly taxing on the orthopedic surgeons.

While replacing or repairing the acetabulum in MIS for instance, the surgeon must avoid or at least minimize damage to ligaments, tendons, muscles, nerves, and other soft tissue. Surgical retractors are used to assist the surgeon in retracing soft tissue to obtain access to the surgical site. Traditional surgical retractors, though, are not shaped and sized to work well through the small incision in MIS.

In short, instruments, and in particular surgical posterior retractors, play a vital role in MIS surgery for hip implantation. It therefore would be advantageous to provide a new method and accompanying instruments for performing a minimally invasive surgery to implant a prosthetic hip.

SUMMARY OF THE INVENTION

The present invention is directed to a method and apparatus for performing minimally invasive hip surgery and, more particularly, to an improved method and apparatus for performing minimally invasive hip replacement surgery for the acetabulum using surgical retractors. These retractors are sized and shaped to be used in the posterior and inferior portions of the surgical site.

The method of the present invention generally comprises the steps of templating the acetabulum to estimate the size of reamer and acetabular components; incising the surgical site with a single incision approximately three to five inches in length; providing surgical retractors adapted to be used in the posterior portion of the surgical site; using the posterior retractors to retract soft tissue at the acetabular joint; dislocating the hip from the acetabulum; providing an acetabular reamer; reaming the acetabulum with the reamer; providing an acetabular shell impaction instrument; inserting and aligning a trial shell into the reamed acetabulum; inserting a trial insert to the trial shell; removing the trial insert and shell; inserting and aligning an implant shell into the reamed acetabulum; impacting the implant shell with the acetabular shell impaction instrument; inserting and impacting an implant insert into the implant shell; and closing the surgical site.

One important advantage of the present invention is that the method and posterior retractors are used in a minimally invasive orthopedic hip surgery. A single, small three inch incision is made at the surgical site on the side on the hip. The method of the present invention, thus, enjoys the benefits of a shorter incision compared to traditional hip surgery that uses a much longer incision. As one benefit, the patient can recover in a much shorter period of time after a MIS. The recuperation time in the hospital can be a few days and significantly reduce the cost to both the patient and hospital. This shortened time period is extremely important to the patient. Further, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Another important advantage of the present invention is that curved surgical retractors are used in a MIS. The curvature of this instrument and shape of the retracting section are specifically designed and adapted to be used in minimally invasive surgical techniques for retracting soft tissue away from the natural acetabulum of a patient.

Another important advantage of the present invention is that the curvature and length of the instrument keep the handle section away from the entrance to the surgical site. In MIS, it is particularly important to maintain a clear and unobstructed access to the surgical site since it is so small, measuring approximately three to five inches in length. In the present invention, the handle section of the retractors extends outwardly and away from the surgical site and, thus, does not obstruct access or visual reference to the site.

The posterior retractor generally comprises a body having two primary sections, a handle section and a retracting section. The handle section is elongated with a length specifically adapted to provide sufficient leverage for soft tissue retraction and to position the hand of the user out and away from the surgical site. A distal section of the handle connects to a curved section that leads to the retracting end. This curved section positions the retracting section at about a 90° angle with the handle section. The retracting section includes an elongated paddle with a straight wall on one side that extends to a curved shoulder and recess located on a distal end. An elongated prong is adjacent the recess and extends upwardly to a flare that forms a second side opposite to the straight wall. The flare has a gradual, smooth curvature that transitions inwardly to form the top portion of the paddle. The paddle includes several critical elements of the invention and is discussed in more detail with reference to the figures.

As another advantage, the posterior retractors can consistently and reliably perform through a small three inch opening in the patient. The shape of the retracting section is specifically sized and shaped to retract and hold tissue in the posterior section of the surgical site. The paddle section, for instance, is designed to rest against the ischium while keeping soft tissue from sagging backing into the operating area. As another example, the prong is sized and shaped to rest against the obturator fossa so the flared section can push soft tissue out of the surgical site.

Further yet, the instrument is easy to use and facilitates the implantation procedure. As such, the posterior retractors can appeal to a wide range of orthopedic surgeons with various skills and experience. Further yet, the training and skill level required to use the instrument and become proficient with it is not overly taxing on the orthopedic surgeon.

BRIEF DESCRIPTION OF THE DRAWINGS

FIG. 4 is a side perspective view of the posterior retractor showing dimensional measurements.

FIG. 5 is a bottom perspective view of the posterior retractor.

DETAILED DESCRIPTION

Figure 2:
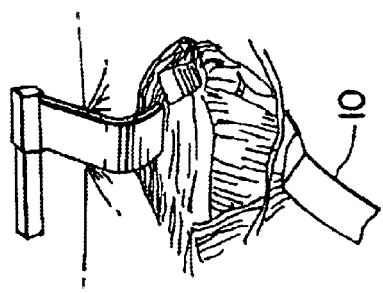
FIG. 2 is a sketch of a MIS surgical site with a posterior retractor of the present invention retracting soft tissue.

The instruments, method, and steps of the present invention are now described in more detail. The method describes the steps to perform a minimally invasive surgery to implant a prosthetic acetabular component 100 into the natural acetabulum 200 of a patient 202. Some of these steps described in the method are known to those skilled in the art and will not be discussed in great detail. Further, one skilled in the art will appreciate that certain steps may be altered or omitted while other steps may be added without departing from the scope of the invention. The novel steps of the present invention, for example, can be applied to total hip arthroplasty, to revision surgeries for total and partial hip replacement, and to other orthopedic hip surgeries using minimally invasive surgical technique.

To facilitate a discussion of the present invention, the method of implanting a prosthetic acetabular component is divided into a plurality of steps or sections. Each of these sections is discussed seriatim.

More specifically, the method of the present invention teaches how to implant a prosthetic acetabular shell 102 and insert 104 into the natural acetabulum 200 using a posterior retractor 10. For illustrative purposes, the discussion focuses on implanting a Converge™ Acetabular System of Centerpulse Orthopedics Inc. of Austin, Tex. This system illustrates one possible acetabular system that can be used. One skilled in the art will appreciate that other, different acetabular systems can also be used with the method and apparatus of the present invention without departing from the scope of the invention.

Templating the Acetabulum

Typically, the side of the acetabulum to be reconstructed is templated. Use of a template enables the surgeon to make an estimation of the size of reamers to be used and the size of acetabular component to be inserted. The acetabulum is templated on the both the anterior-posterior (A/P) and lateral radiographs. The hemisphere of the acetabular component is aligned with the mouth of the bony, natural acetabulum while simultaneously avoiding any osteophytes. On the A/P radiograph, the acetabular component should rest on the floor of the cotyloid notch and may touch the illoischial line. Further, the component should have a maximum lateral opening of about 40°. On the groin lateral radiograph, the cup size selected should contact the anterior and posterior rim of the bony, natural acetabulum and the medial subchondral bone. A correct position of the acetabular component will anatomically reproduce the center of rotation of the femoral head. If a bony defect is identified, use the correctly placed template to measure for proper size of the acetabular component and determine any need for bone graft.

Figure 1:
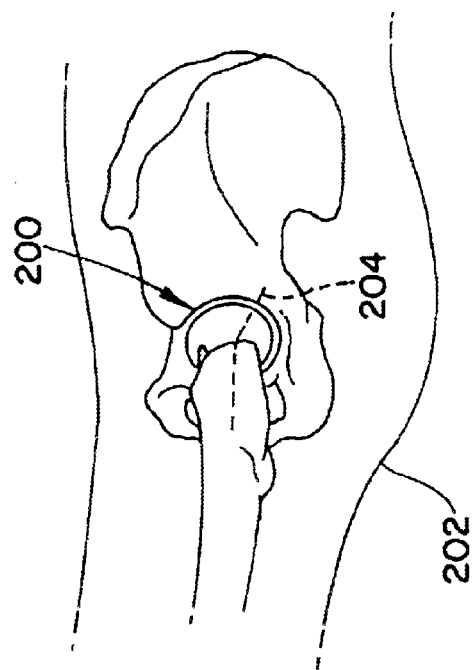
FIG. 1 is a sketch of a patient showing a femur and femoral head positioned in the acetabulum with an MIS incision marked along the hip.

Incising the Surgical Site (See FIG. 1)

A relatively small, single minimally invasive incision 204 is made at the surgical site. A minimally invasive incision 204 for this procedure has a length from about 2½ inches to about 4 or 5 inches. The incision 204 is slightly curved or straight, commences near the vastus tubercle, and continues toward the greater trochanter and posterior inferior spine. The incision should be carried down through subcuntaneous tissue and fascia lata. Any muscle tissue should be gently split in line with its fibers. At this time, a leg length measurement can be taken using techniques known in the art.

Providing Posterior/inferior Retractors (See FIGS. 4–8)

The posterior retractor of the present invention has an elongated, flat, thin body with two primary sections, a handle section and a retracting section. The handle section is elongated and adapted to be gripped with a hand. A smooth curved section transitions the handle section to the retracting section. The retracting section has an enlarged paddle with a relatively straight wall on one side and flare oppositely disposed on the other side. The flare curves outwardly and leads to an elongated prong that curves outwardly and away from the paddle and handle section. The bottom of the paddle includes a recess and shoulder that connect to the straight wall. The posterior retractor of the present invention is discussed in more detail with reference to FIGS. 4–8.

Exposing the Acetabular Joint & Dislocating the Hip from the Acetabulum

Next, the knee is flexed, and the leg is internally rotated. Using a hot knife, the piriformis, short external rotators, quadratus femoris, and some posterior capsule are incised off the posterior trochanter to expose the lesser trochanter. Dislocation of the hip can now occur. A bone hook or skid may be used to avoid excess torsion on the femoral shaft.

At this time, retractors may be placed, for example under the femoral head or lesser trochanter, in order to achieve visualization for proper transection of the femoral neck if this procedure is desired at this time. If such transection occurs, the femoral neck should be transected at the templated level. Then retract the femur in an anterior direction to expose the acetabulum. Care should be taken to protect the sciatic nerve.

A retractor can be placed on the pelvis to hold the femur in an anterior position to the acetabulum. The capsule can be retracted in the posterior using retractors or pins. After the labrum and osteophytes are removed, at least a partial view of the acetabulum should be available.

Retracting the Surgical Site with Posterior Retractors (See FIG. 2)

The posterior retractor of the present invention is particularly advantageous for retracting soft tissue in the posterior/inferior regions of the surgical site. The prong should be positioned to engage the obturator fossa or cotyloid notch. In this position, the size and shape of the flare will help keep soft tissue from sagging back into the surgical site and obstructing access to the bottom of the wound channel. Further, the paddle can be positioned to rest on or against the ischium. Compared to traditional designs, the paddle has an extended or elongated shape that will help keep soft tissue from sagging back into the surgical site and obstructing access to the bottom of the wound channel. As another advantage, the paddle, in this position, is adapted to protect the sciatic nerve. Specifically, the body of the paddle shields the sciatic nerve damage during the surgical procedure. Further, multiple posterior retractors can be placed to retract soft tissue in the posterior region. These retractors can include a left and/or a right posterior retractor.

Providing an Acetabular Reamer

An acetabular reamer is provided to ream the natural acetabulum. The reamer is designed and adapted to be used with minimally invasive surgical techniques of the acetabulum. Specifically, the reamer is shaped to fit through the small incision at the surgical site. Further, the reamer is angled so the distal end properly engages the natural acetabulum with the correct angular orientation and without disrupting the incision and surrounding soft tissue.

Reaming the Acetabulum

Reaming of the acetabulum should begin with a reamer that is two sizes smaller than the preoperatively selected acetabular component size. A smaller reamer ensures that the fit does not exceed the anterior-posterior diameter. Of course, the reamer should not be so small that excessive anterior or posterior reaming occurs.

After an appropriately sized reamer is connected to the acetabular reamer, reaming should begin transversely toward the cotyloid notch. The ridges of the horseshoe (or medial osteophytes) should be removed. Reaming then continues in the position of desired anteversion while simultaneously creating a hemisphere. Larger reamers are used until the anterior and posterior rim of the acetabulum is contacted. The reamer should not be sunk below the superior rim of the bony acetabulum or reamed through the cortical bone of the cotyloid notch. Cancellous bone will be evident where the horseshoe ridges have been removed. The proper size trial shell should be selected according to the size of the reamer.

Providing an Acetabular Shell Impaction Instrument

An acetabular shell impaction instrument is provided to align and then impact the acetabular shell into the natural acetabulum. The instrument is designed and adapted to be used with minimally invasive surgical techniques of the acetabulum. Specifically, the instrument has a curved shape to fit through the small incision at the surgical site and precisely impact the implanted shell at the correct angular orientation. Further, this curvature enables the instrument to engage the shell in the acetabulum without disrupting the incision and surrounding soft tissue. Further yet, the instrument is adapted to move and align the acetabular shell while it is positioned in the acetabulum. It is important to position properly the shell before it is impacted and permanently seated in the acetabulum.

Inserting a Trial Shell into the Acetabulum

The acetabular shell impaction instrument keys off the dome of the trial shell and is threaded or engaged in place. The instrument may offer anteversion and abduction references and rotational control. Preferably, the distal end of the instrument is adapted to mate with both the trial shell and implant shell in one single orientation. To connect the components, the distal end of the instrument is keyed and threadably attached to the trial shell. One skilled in the art will appreciate that the instrument, inserts, and shells can connect in various ways.

After the trial shell is inserted into the acetabulum, its position is verified through a trial window. The edge of the trial shell should be level with the anterior-inferior margins of the acetabulum and should completely fill the anterior-posterior bony acetabulum. The instrument can be used to move and align shell while it is positioned in the acetabulum. At this time, the trial shell can be manually tested to ensure that it is stable. If the trial is loose, then use the next larger size. If the trial is too tight, then ream the rim of the acetabulum. Importantly, the trial shell should be stable before selecting a similarly sized acetabular implant shell.

Inserting a Trial Insert into the Trial Shell

Now, the trial insert is ready to be placed in the trial shell. An instrument is engaged in the rim of the trial insert and it is positioned inside the cavity of the trial shell. The trial insert contains a captured screw at the apex and can be threaded into the dome of the trial shell with a screwdriver or other tool. The trial components should be checked for proper fit and size.

At this point, the trials are removed from the surgical site. One skilled in the art, though, will appreciate that the trials could be temporarily left inserted to the natural acetabulum to articulate with a trial femoral prosthesis in a total hip replacement surgery.

Figure 3:
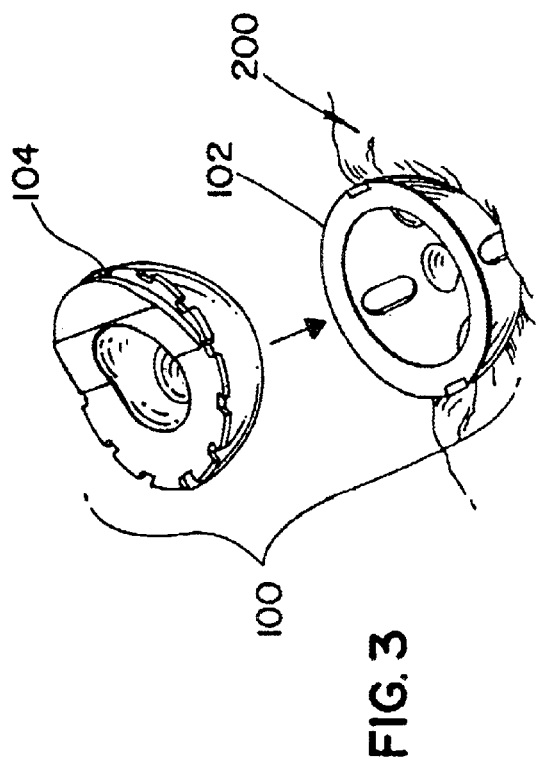
FIG. 3 is a perspective view of an acetabular insert being connected to an acetabular shell that is embedded into the natural acetabulum of a patient.

Inserting an Implant Shell into the Acetabulum (See FIG. 3)

Some implant shells may be provided with flared rims and outer bone engaging spikes. In order to insert such a shell, cancellous bone slurry may be added within the acetabulum to fill existing bone cysts and provide an interface layer. Addition of this slurry typically occurs in total hip arthroplasty situations.

The acetabular implant shell is positioned into the acetabulum using the same acetabular shell impaction instrument used with the trial shell. Specifically, the distal connection end of the instrument is engaged and connected to the shell. The shell is partially inserted into the acetabulum until the rim begins to engage bone. The implant is then positioned with the instrument to the desired angular orientation, such as abduction and anteversion. Preferably, the shell is positioned with 20° to 25° of anteversion and with an abduction angle of about 35° to 45°. The anteversion can be verified using techniques known to those skilled in the art. The proximal impaction end of the instrument is then impacted with a mallet or similar instrument. Force from the mallet is transferred from the instrument to the shell as it is driven and permanently seated into the natural acetabulum. The shell should be driven into the acetabulum until the outer fixation spikes centrally engage into cancellous bone.

Removing Screw-holes & Inserting Dome Plug

The implant shell may be provided with screw-hole seals and a dome plug. In this instance, after the shell is properly seated in the acetabulum, one or more of the screw-hole seals may be removed with a screw-hole extracting instrument. This instrument is inserted through the incision and into the indentation of the screw-hole seal. Leverage is used to dislodge the screw-hole seal from the shell. It should be noted that screw-hole seals can be dislodged at the back table before the shell is seated in the acetabulum. By contrast, the dome plug should be installed before the insert is impacted.

Drilling Holes & Attaching Bone Screws

Next, a drill bit is connected to a flexible driver and is positioned into the selected screw hole at an angle up to about 16°. As the hole is drilled, care should be taken to protect the sciatic nerve and superior gluteal artery. A depth gauge may be inserted into the drilled holes to determine the depth for a corresponding bone screw. If desired, a tapping bit may be connected to the driver to tap the hole.

A bone screw is connected to a U-joint screwdriver and positioned into the drilled hole. The screw should be seated into the countersunk holes of the shell so the acetabular insert can properly snap into the shell.

Inserting & Impacting Insert into Shell (See FIG. 3)

Various inserts known to those skilled in the art (such as standard, hooded, and protrusion inserts) can be inserted into the implant shell. Once the appropriate size and style insert is selected, the insert is connected to an instrument. The insert is positioned into the cavity of the shell and should be rotated to align with the antirotational pegs on the shell. A surgical mallet is used to strike the proximal end of the instrument to seat the insert into the shell.

Closing Surgical Site

Once the insert is firmly connected to the shell, all instruments and devices are removed from the site. The acetabular shell and insert should now be properly positioned. Closure of the site may occur with well known techniques, such as posterior and anterior lateral approaches. Further, this disclosure will not discuss post-operative protocol or rehabilitation as such procedures are known in the art and tailored to meet the specific needs of the patient.

Detailed Description of Posterior Retractor Instrument

One important advantage of the present invention is that the instrument is specifically designed and adapted to be used in minimally invasive surgical techniques for retracting soft tissue at the posterior/inferior aspect of the surgical site while implanting a prosthetic acetabular shell into the natural acetabulum of a patient. This design includes critical sizes and shapes that will be discussed in connection with the figures.

FIGS. 4–8 show the posterior retractor 10 of the present invention has an elongated, flat, thin body with two primary sections, a handle section 12 and a retracting section 14. The handle section extends from a proximal section 16 to a distal section 18 and is elongated with a length of about 10.5 inches (and specifically 10.87 inches) and a width that tapers, but generally is between about 0.5 inches to 1.5 inches. The length of the handle is one critical element to the invention. Specifically, the length is long enough to position the proximal end of the handle section away from the surgical site in a MIS. As such, a hand holding the posterior retractor at or near the proximal end of the handle section will not obstruct access to the surgical site during the operation. Also, the length of the handle provides great leverage to retract the posterior soft tissue from the surgical site. Preferably, the handle has a length equal to about twice the length of the retracting section.

The proximal end 16 of the handle section has a smooth curved end, and the distal end 18 of the handle section has a smooth curved section 20 that transitions the handle section 12 to the retracting section 14. Preferably, the handle and retracting sections form an angle θ (FIG. 7) that is about 90° (see FIG. 4 for exact dimensional measurements). This angle is another critical element to the invention. Specifically, this angle enables the retracting end to engage and retract soft tissue through the small incision in MIS while, at the same time, enables the handle section to be positioned away from the opening to the surgical site. As such, the handle section will not obstruct the opening to the surgical site during the surgical procedure.

The retracting section 14 has an enlarged paddle 30 with a relatively straight wall 32 on one side and flare 34 oppositely disposed on the other side. Straight wall 32 leads to a rounded shoulder 36 that dips to a well or recess 38. On the other side of the straight wall, flare 34 curves outwardly and leads to an elongated prong 40 that curves outwardly and away from the paddle 30 and handle section 12.

Figure 8:
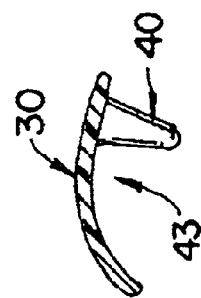
FIG. 8 is a view taken along the lines A—A of FIG. 6.
Figure 7:
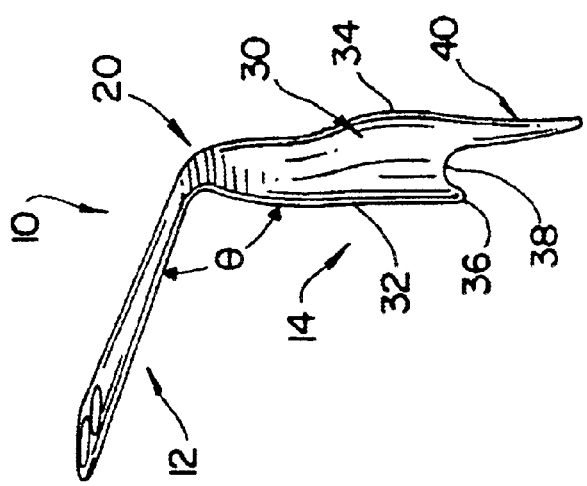
FIG. 7 is a side perspective view of the posterior retractor.
Figure 6:
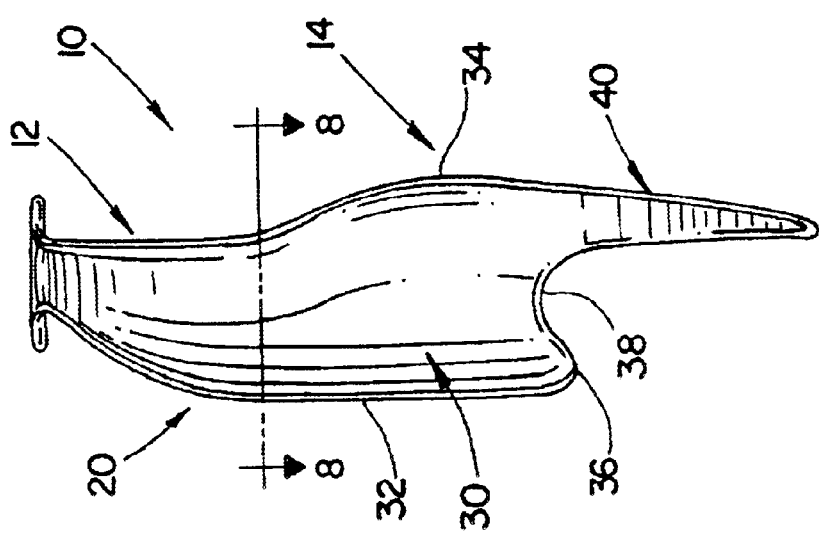
FIG. 6 is a front view of the posterior retractor.

Preferably, the paddle 30 tapers outwardly or widens as it moves away from the curved section 20. Further, paddle 30 has a length of about 3–3.5 inches and a width about 1.0–1.5 inches. This width is larger than the width of the handle section 12. Further yet, as best shown in FIGS. 5 and 8, the body of the paddle has a rounded or curved shape that forms a shallow channel 43. The shape and size of the paddle are critical elements to the invention. Specifically, the paddle can rest on or abut against the ischium during the surgical procedure. At the same time, the specific length and width of the paddle enables it to retract a large amount of soft tissue away from the surgical site. As another important feature, the paddle is shaped and sized to protect the sciatic nerve of the patient while abutting against the ischium. The sciatic nerve is an extremely important nerve that passes through the surgical site, and this nerve must be shielded and protected to not compromise the health of the patient during MIS.

Flare 34 curves or swells outwardly along the side of the paddle and then smoothly transitions back to the prong 40. The flare is a critical element of the invention. Specifically, this flare is sized and shaped to retract soft tissue and keep it from sagging back into the surgical site and obstructing access to the wound channel.

Prong 40 has an elongated, thin rectangular shape that tapers as it extends downwardly from the body of paddle 30. The prong has a length about 1.25 inches to about 2.5 inches, and preferably 1.6 inches. Simultaneously, the prong smoothly curves away from the handle section 12. Preferably, handle section 12 and a center of prong 40 forms an angle greater than 90° (see FIG. 4 for dimensional measurements). This length, curvature, and angle are critical elements to the invention. Specifically, the prong can engage and leverage against the obturator fossa or cotyloid notch during the surgical procedure. Further, gradual curvature of the prong follows the natural shape of the caudal and medial profiles of the patient. In short, the specific dimensions and shape of the prong enable it to be in this position.

The posterior retractor may be provided as a left side posterior retractor or a right side posterior retractor. These two are essentially mirror images of each other. The left and right side retractors provide an important benefit during the surgical procedure. The left side retractor is particularly adapted to be utilized on the left side of the posterior of the surgical site, and the right side retractor is particularly adapted to be utilized on the right side of the posterior. A surgeon, thus, may select the appropriate left or right retractor depending on the side in the posterior to retract soft tissue.

Preferably, the retractors are constructed of a single steel body that is durable and strong enough to leverage soft tissue and the like away from the surgical site. Particular steels suited for this use are known in the art.

It should be emphasized that although the method of the present invention was described with a specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention. Further, although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for using minimally invasive surgery to implant a prosthetic acetabular shell and insert into a natural acetabulum, comprising of:
   incising a hip with a minimally invasive incision;
   providing a posterior retractor having a handle section and a retracting section, the retracting section includes a paddle with a flare on one side and an elongated prong that extends downwardly from the flare;
   positioning the prong against the obturator fossa and the paddle against the ischium;
   retracting soft tissue with the retracting section;
   positioning the acetabular shell and insert into the natural acetabulum; and closing the incision.

2. The method of claim 1 wherein the step of incising a hip creates the minimally invasive incision with a length of about 2½ inches to about 4 to 5 inches.

3. The method of claim 2 further comprising the step of providing the paddle with a body having a width larger than a width of the handle section.

4. The method of claim 3 further comprising the step of shielding a sciatic nerve with a paddle.

5. The method of claim 4 further comprising the step of providing a flare with a smooth curved shape.

6. The method of claim 5 further comprising the step of providing the paddle with a generally straight walled section on the other side oppositely disposed from the flared section.

7. The method of claim 6 further comprising the step of providing the prong with a body that curves away from the handle section.

8. The method of claim 1 wherein the prong has a length of about 1.6 inches.

9. A method for implanting a prosthetic acetabular component into a natural acetabulum of a patient, the method comprising the steps of:
   incising a hip to produce an incision with a length of about 2½ inches to about 5 inches to create a surgical site with access to the natural acetabulum;
   providing a posterior retraction instrument having a handle section and a retracting section, wherein the retracting section includes paddle with a flare along a first side and a prong extending downwardly from the flare, the prong having a curved shape;
   positioning the posterior retraction instrumentation in a posterior portion of the surgical site;
   retracting soft tissue with the retracting section;
   positioning the acetabular component into the natural acetabulum; and
   closing the surgical site and incision.

10. The method of claim 9 further comprising the step of providing the retracting section at an angle of about 90° with respect to the handle section.

11. The method of claim 10 further comprising the step of providing the handle section with a length of about twice a length of the retracting section.

12. The method of claim 11 further comprising the step of providing the paddle with a curved shape forming a shallow channel.

13. The method of claim 10 further comprising the step of providing the handle section with a length of about 10.5 inches and the paddle with a length of about 3.0–3.5 inches.

14. The method of claim 9 further comprising the step of abutting the paddle against an ischium and the prong against a cotyloid notch.

15. The method of claim 14 further comprising the step of shielding a sciatic nerve with a paddle.

16. A method for implanting a prosthetic acetabular component into a natural acetabulum of a patient, the method comprising the steps of:
   incising the patient with an incision from about 2½ inches to about 5 inches to provide surgical access to the natural acetabulum;
   preparing the natural acetabulum to receive the acetabular component;

providing a retractor having an elongated handle section connected to a retracting section, the retracting section including a paddle and a curved prong extending outwardly from the paddle;

positioning the retractor in a posterior aspect of the incision so the paddle abuts an ischium and shields a sciatic nerve;

positioning the acetabular component into the natural acetabulum; and closing the incision.

17. The method of claim 16 further comprising the step of positioning the prong against a cotyloid notch of the patient.

18. The method of claim 16 further comprising the step of providing the handle section to form an angle of about 90° with the retracting section.

19. The method of claim 16 further comprising the step of providing the retracting section with a curved shoulder at a distal portion of the paddle.

20. The method of claim 19 further comprising the step of providing the paddle with a recess adjacent one side and a curved flare adjacent another side of the paddle.

* * * * *